United States Patent [19]
Chroboczek et al.

[11] Patent Number: 6,083,720
[45] Date of Patent: Jul. 4, 2000

[54] DODECAHEDRAL ADENOVIRAL PROTEIN COMPLEX, COMPOSITION CONTAINING SAME AND USES THEREOF

[76] Inventors: Jadwiga Chroboczek, 22 cours de la Libération, 38100 Grenoble; Pascal Fender, 11 rue Turenne, 38000 Grenoble, both of France

[21] Appl. No.: 09/068,650

[22] PCT Filed: Nov. 13, 1996

[86] PCT No.: PCT/FR96/01790

§ 371 Date: Jul. 31, 1998

§ 102(e) Date: Jul. 31, 1998

[87] PCT Pub. No.: WO97/18317

PCT Pub. Date: May 22, 1997

[30] Foreign Application Priority Data

Nov. 13, 1995 [FR] France ................................ 95 13406
Apr. 18, 1996 [FR] France ................................ 96 04843

[51] Int. Cl.[7] .......................... C12P 21/00; C12P 21/02; C12N 15/861; C12N 15/63; C12N 5/10
[52] U.S. Cl. .................. 435/69.1; 435/320.1; 435/455; 435/456; 435/235.1; 435/325; 435/366; 435/371; 435/372; 530/350; 536/23.1; 536/24.5
[58] Field of Search ................................ 435/69.1, 320.1, 435/5, 6, 69.3, 455, 456, 235.1, 325, 366, 371, 372; 424/93.2, 93.6, 204.1, 233.1; 530/350; 536/23.1, 24.5

[56] References Cited

FOREIGN PATENT DOCUMENTS

WO 94/17832   8/1994   WIPO .

OTHER PUBLICATIONS

Rabinovich et al., Science, vol. 265, pp. 1401–1404, Sep. 2, 1994.
Cohen, Science, vol. 265, pp. 1371–1373, Sep. 2, 1994.
Norrby et al., Virology, vol. 36, pp. 201–211, 1968.
Anderson, Nature, vol. 392, pp. 25–30, Apr. 30, 1998.
Verma et al., Nature, vol. 389, pp. 239–242, Sep. 18, 1997.
Ross et al., Human Gene Therapy, vol. 7, pp. 1781–1790, Sep. 10, 1996.
Nature Biotechnology, vol. 15, pp. 519–524, Jun. 15, 1997.
Gura, Science, vol. 270, pp. 575–577, Oct. 27, 1995.
Orkin et al., "Report and Recommendations of the Panel to Assess the NIH Investment in Research on Gene Therapy", Dec. 7, 1995.
Karayan, Lucie et al., "Oligomerization of Recombinant Penton Base of Adenovirus Type 2 and Its Assembly with Fiber in Baculovirus–Infected Cells", *Virology*, vol. 202, 1994, pp. 782–795.
Boudin, Marie–Laure et al., "Assembly of Adenovirus Penton Base and Fiber", *Virology*, vol. 116, Jan. 30, 1982, pp. 589–604.

*Primary Examiner*—David Guzo
*Attorney, Agent, or Firm*—Alston & Bird LLP

[57] ABSTRACT

A native or recombinant adenoviral protein complex, a pharmaceutical composition containing said protein complex, and the uses thereof for treating and preventing human and animal diseases, are disclosed. Said adenoviral protein complex consists of either 12 pentons each including at least one fiber and a penton base, but no other element from an adenovirus genome, said fiber(s) and said penton base being derived from one or more adenoviruses, said pentons being bound by the penton bases and forming a proteolytic enzyme-stable dodecahedral structure, said complex having a molecular weight between $4.8 \times 10^6$ and $6.6 \times 10^6$, and such complexes being known as dodecahedron-penton complexes; or 12 penton bases but no other element from an adenovirus genome, said penton bases being derived from one or more adenoviruses and forming a proteolytic enzyme-stable dodecahedral structure, said complex having a molecular weight between $3.2 \times 10^6$ and $4 \times 10^6$, and such complexes being known as dodecahedron-base complexes.

27 Claims, 12 Drawing Sheets

High 15% sucrose — Low 40% sucrose

Penton base

Fibre

*A*

High — Low

0 minute 5 minutes 10 minutes

Zoom X 1.9

20 minutes 30 minutes 45 minutes

DODECAHEDRAL ADENOVIRAL PROTEIN COMPLEX, COMPOSITION CONTAINING SAME AND USES THEREOF

The present invention relates to a native or recombinant adenoviral protein complex, to a pharmaceutical composition comprising the said protein complex, and to their application in the treatment (medicaments) and prevention (vaccines) of human and animal diseases. The said protein complex is especially capable of dispensing nucleic sequences, proteins, peptides or chemical substances of interest to suitable target cells.

The present invention likewise relates to expression vectors of the said protein complex.

The adenoviruses form a family of DNA animal viruses gathering together more than 90 serotypes infecting different species, including nearly 50 different human serotypes. The cellular tropism of the adenoviruses results in the infection of the respiratory, gastrointestinal and urinary tracts and of the eyes.

These viruses are responsible for 3% of all infections in man, for 10% of infantile pneumonias and for 15% of intestinal infections in children.

The adenovirus particle is relatively complex and comprises several sub-structures; in particular, the external part or capsid is formed mainly of three proteins: the hexon, the penton base and the fibre (see FIG. 1).

The penton, a non-covalent complex formed of a trimeric protein, the fibre, and of a pentameric protein, the penton base, forms the vertices of the viral icosahedron.

Each of the two proteins forming the penton play a fundamental role in infection: the fibre allows the attachment of the virion to a cell receptor; the penton base allows the internalization of the virion, probably owing to the interaction with the cell integrins (linkage with the integrins, vitronectin and fibronectin receptors, by the intermediary of the arg-gly-asp sequence present at the level of the penton base) (Wickham et al., Cell, 1993, 73, 309–319). In addition, observations exist which suggest that the penton base has an endosomolytic activity, allowing the escape into the cytoplasm of molecules co-internalized with the virus (Seth et al., Virus Attachment and Entry into Cells, 1986, Ed. R. L. Crowell & K. Lonberg-Holm, 191–195).

The binding of the adenoviruses to the cells and their internalization are thus two events which are distinct but which cooperate.

The capacity to infect various quiescent cells makes the adenovirus a vector of choice for gene therapy.

The methods currently employed are based on the repeated administration of recombinant adenoviruses, which are deficient for replication, carrying the target gene (PCT International Applications WO 95/02697 and WO 95/14101, in the name of Rhone-Poulenc Rorer SA).

However, the recommended treatments with such deficient adenoviruses have at least the following disadvantages:

risk of restoration in trans of the pathogenicity of the recombinant virus in a subject treated and simultaneously infected by a wild adenovirus;

immune and inflammatory reactions during the repeated administration of the recombinant adenovirus, due to the massive introduction of viral particles bringing in foreign proteins, which curb their use as a gene therapy vector in man.

To avoid such disadvantages, it has been proposed to use only the penton or the penton base, independently of the rest of the genome of the adenovirus, to facilitate the transfer of exogenic genes into host cells (PCT International Application WO 94/17832, in the name of The Scripps Research Institute). Although such an approach has advantages with respect to the recombinant adenoviruses which are deficient for replication, such structures (penton or penton base) are fragile, especially the penton base, which can be destroyed by proteolysis.

As a consequence, the Applicant has the aim of providing a vector which can be used in gene therapy which answers the needs of practice better than the vectors of the prior art; such a vector does not have either the disadvantages of recombinant adenoviruses, or the fragility of the penton or of the penton base, such as specified above.

The present invention relates to an adenoviral protein complex, characterized in that it is formed either:

of 12 pentons, each comprising at least one fibre and one penton base, with the exclusion of any other constitutive element of the genome of an adenovirus, which fibre(s) and penton base are derived either from the same adenovirus, or from different adenoviruses, the said pentons being bound by the penton bases and forming a dodecahedral structure, stable to proteolytic enzymes, which complex has a molecular weight of between $4.8 \times 10^6$ and $6.6 \times 10^6$; such complexes are called below dodecahedron-fibre or dodecahedron-penton complexes;

or of 12 penton bases, with the exclusion of any other constitutive element of the genome of an adenovirus, which penton bases are derived either from the same adenovirus, or from different adenoviruses, and form a dodecahedral structure, stable to proteolytic enzymes and in that it has a molecular weight of between $3.2 \times 10^6$ and $4 \times 10^6$; such complexes are called below dodecahedron-base complexes.

The said complexes thus do not comprise any element of the genome of one of the said adenoviruses. The said native or recombinant dodecahedral protein complexes facilitate the transfer of foreign genes, of nucleic acid sequences, of proteins, of peptides or of chemical molecules into the target cells.

According to the invention, the said adenoviruses are selected from human adenoviruses and especially type 2 adenovirus (Ad2), type 3 adenovirus (Ad3), type 5 adenovirus (Ad5), type 4 adenovirus (Ad4), type 7 adenovirus (Ad7), type 9 adenovirus (Ad9), type 11 adenovirus (Ad11), type 15 adenovirus (Ad15), or the enteric adenoviruses (Ad40 and Ad41) and the avian adenoviruses.

According to an advantageous method of production of the said recombinant dodecahedral protein complexes, at least one of its constituents (base and/or fibre) can be modified to increase the affinity with respect to a particular cell type.

Such a protein complex modified in this way does not show any decrease in its properties of attachment to the target cell and of internalization in the said cell, on the one hand with respect to the wild adenovirus and on the other hand with respect to the complex according to the invention in which the said constituents are not modified.

For example, a sequence of attachment to other receptors, such as the CD4 receptor present on T cells, can be incorporated into the fibre by recombinant DNA techniques (ligand-fibre combination).

It is possible to cite as examples of appropriate ligands the V3 loop of the gp120 of HIV (linkage with CD4), transferrin (binding to the transferrin receptor), the LDLs (linkage to the LDL receptors), deglycosylated proteins and antibodies.

A preferred dodecahedral protein complex according to the invention is formed either of 12 penton bases, corresponding to those of an adenovirus selected from the group formed by Ad3, Ad4, Ad7, Ad9, Ad11 and Ad15, or of 12 pentons whose fibre sequences correspond to those of any one of the abovementioned human, enteric or avian adenoviruses and whose penton base sequences correspond to those of an adenovirus selected from the group formed by Ad3, Ad4, Ad7, Ad9, Ad11 and Ad15, preferably to those of type 3 adenovirus (Ad3).

Another dodecahedral protein complex preferred according to the invention is formed of 12 pentons, whose fibre sequences correspond to those of type 2 adenovirus (Ad2) or of type 5 adenovirus (Ad5) and whose penton base sequences correspond to those of type 3 adenovirus (Ad3).

The use of the adenoviral protein complex according to the invention in the place of the adenovirus virion eliminates the danger of accidental infection by the adenovirus and is accompanied by much weaker immune and inflammatory reactions; in addition, it is particularly stable and the presence of 12 penton bases significantly increases the lysis rate of the endosomes (more rapid cytoplasmic passage) with respect to a structure only containing one penton or one base.

According to another advantageous method of production of the said recombinant adenoviral protein complex, it additionally comprises at least one hexon or viral protein.

The present invention likewise relates to a pharmaceutical composition, characterized in that it essentially comprises an adenoviral protein complex according to the invention and at least one other chemical substance.

According to an advantageous method of production of the said composition, the said other chemical substance is selected from the group formed by nucleic acid sequences, proteins, peptides and pharmacologically active chemical substances.

When the chemical substance is a protein, the latter preferably has immunoprotective and antigenic properties, and is particularly well adapted to the preparation of a vaccine.

When the chemical substance is a pharmacologically active chemical substance, it is especially selected from the cell toxins, such as anticancer agents and especially anthracyclines.

In this last case, the composition according to the invention has the advantage of avoiding the resistance mechanism usually encountered with anticancer agents. In fact, the development of resistance to an antitumour chemotherapy forms a major obstacle to the treatment of human cancers. This resistance is due in large part to the induction of the activity of a very effective extracellular pump which does not allow the transport of the pharmacologically active substance into the interior of the cell. However, surprisingly, the composition according to the invention allows the introduction of the pharmacologically active substance into the cell by getting round this resistance mechanism.

When the active substance is a nucleic sequence, it is selected from genes which code for a polypeptide having a therapeutic activity, anti-sense sequences and ribozymes.

In the case of a coding sequence, it additionally comprises an active promoter for the expression of the polypeptide.

According to an advantageous embodiment of this production method, the promoter is selected from the group formed by constitutive promoters and inducible promoters.

The said active chemical substance can be bound to the adenoviral protein complex according to the invention in at least two different fashions:

either by the intermediary of a temporary bond, such as an ionic or hydrophobic bond, which can be destroyed and thus allows the passage of the active substance into the nucleus (expression of a gene at the level of the nucleus) (ligand selected from the substances capable of producing an ionic or hydrophobic bond with the said active substance);

or by the intermediary of a stable bond, such as a covalent bond, for example, which retains the active substance in the cytoplasm; such a type of bond is of particular interest for the preparation of vaccine compositions (persistence of the active substance in the cytoplasm) (ligand selected from substances capable of producing a covalent bond with the said active substance).

In fact, the said chemical substance, especially a nucleic acid sequence, a protein or a peptide, can be combined (covalently or non-covalently) with a suitable ligand.

Among suitable ligands, peptides can be mentioned whose N-terminal part comprises the N-terminal amino-acid sequence of an adenovirus fibre of any serotype (zone of attachment to the protein complex according to the invention) and whose C-terminal part comprises:

a polylysine (sequence which allows the attachment of the active substance, especially when it is a nucleic acid), a polyarginine, a part or the complete sequence of a core protein of any adenovirus (VII protein, A protein of human adenoviruses or homologous proteins encountered in adenoviruses present in other animals), a cysteine, or a transferrin/poly-L-lysine complex, which combines with the said nucleic sequence or with the said protein to form a conjugate.

Such peptides, called bifunctional peptides, are bound by their N-terminal part to the adenoviral protein complex according to the invention and by their C-terminal part to a plasmid DNA to be transferred.

For example, the peptide comprising a polylysine at its C-terminal end allows a bond of ionic type, a peptide comprising a cysteine at its C-terminal end allows a bond of covalent type and the combination of a nucleic acid or protein and transferrin/poly-L-lysine conjugate, in which the transferrin is bound to the transferrin receptors on the surface of target cells, with the protein complex according to the invention allows better transport of the chemical substance of the endosomes towards the cytoplasm.

Another method of transfer of nucleic sequences or of proteins is possible, using an avidin-biotin complexation reaction and an anti-fibre, anti-penton base or anti-dodecahedral protein complex antibody. Such a composition employs: a dodecahedral protein complex according to the invention, an antibody which reacts either with the fibre or with the penton base, or with the dodecahedral protein complex, but does not inhibit the functionality of the said protein complex, a vector containing a nucleic sequence of interest in which at least one nucleotide is biotinylated, possibly bound to a marker sequence or a biotinylated protein and a chimeric protein consisting of protein A bound to streptavidin (SA-PA). From the fact that a nucleotide or the protein is biotinylated, they can be bound to the SA-PA chimeric protein. In such a composition, the biotinylated DNA or the biotinylated protein is bound to the SA-PA chimeric protein; the DNA complex bound to the SA-PA is then bound via the PA moiety to an antibody which reacts either with a fibre, or with a penton base, or with the dodecahedral protein complex. The complex product thus formed comprising PA-immobilized antibody-dodecahedral protein complex is bound, by the intermediary of the protein complex, to the specific receptors of the latter, expressed on the surface of the target cells.

In all cases, the exogenous nucleic acid sequence, the protein of interest or any other chemical substances included in or combined with the composition according to the invention penetrates into the cell (internalization) by the intermediary of the dodecahedral protein complex according to the invention.

Surprisingly, the dodecahedron-receptor cell interaction increases, significantly, both the internalization of the composition according to the invention and the permeability of the endosomes, which increases, significantly, the passage of exogenous nucleic acid, of the protein of interest or of any other chemical substance, of the endosomes towards the cytoplasm, in comparison with the use of a composition only containing a sole penton.

According to another method of production of the said pharmaceutical composition, it comprises, in addition, at least one pharmaceutically acceptable vehicle.

Among pharmaceutically acceptable vehicles, it is in fact possible to mention vehicles adapted to the route of administration studied, such as water, salt, dextrose, glycerol, ethanol, vpolyeble oils, propylene glycol, polyethylene glycol, benzyl alcohol (parenteral administration or liquid preparations), liposomes or other polymers (for example cationic polymers).

Such compositions may, in addition, contain wetting or emulsifying agents, isotonic agents, dissolving agents, stabilizers, colorants, antiseptic agents and the like.

According to the invention, the said active chemical substance is either included in the said dodecahedral protein complex according to the invention, or combined with the said complex; in both cases it can be free or bound to the said complex.

The compositions according to the invention can be administered in different forms and by different routes, such as the pulmonary route (aerosol), intraperitoneal route, parenteral route or surgical implant.

The compositions according to the invention have numerous applications as medicaments, in human and veterinary medicine:

in human and animal gene therapy, especially in the hereditary illnesses involving the respiratory epithelium, such as emphysema or mucoviscidosis, as antiviral agents (anti-sense sequences or ribozymes), as immunogenic or vaccinal agents, as anti-bacterial, anti-cancer agents and the like.

The present invention likewise relates to a composition essentially comprising a dodecahedral adenoviral protein complex, such as defined above, and a chemical substance selected from nucleotide sequences, proteins and pharmacologically active chemical substances, as a medicament or as a vaccine.

The present invention likewise relates to a composition comprising a dodecahedral adenoviral protein complex, such as defined above, and a chemical substance selected from the nucleotide sequences, the immunogenic substances and the anticancer substances, for use thereof in the treatment of human or animal illnesses involving cells expressing specific receptors of adenovirus fibres and/or of cells expressing integrin receptors, especially $\alpha_{v}\beta_{3}$ or $\alpha_{v}\beta_{5}$ integrins, such as epithelial cells, endothelial cells, blood platelets, lymphoid cells and cancerous cells and liberating an efficacious quantity of the said active chemical substance to the said cells.

The present invention in addition relates to a process for the preparation of the said dodecahedral adenoviral protein complex according to the invention.

Such a process preferably comprises the following steps:

(1) the separate or simultaneous cloning of the gene(s) coding for the fibre(s) of an adenovirus, the gene coding for the penton base of an adenovirus and possibly the gene coding for the hexon of an adenovirus, the said genes being either from the same adenovirus, or from different adenoviruses, in at least one baculovirus vector, to obtain several recombinant plasmids containing either one gene, or two genes (simultaneous expression of the two fibres in the case of an adenovirus containing two fibres per penton) or to obtain a recombinant plasmid simultaneously containing two genes (or three genes in the case of the use of an adenovirus containing two fibres per penton); in the latter case, the baculovirus vector used comprises a double or triple expression cassette, while in the case where the protein complex according to the invention additionally comprises at least one hexon, the said baculovirus vector can comprise a multiple expression cassette;

(2) the co-transfection of the recombinant plasmid(s) and of a linearized baculovirus DNA fragment in an insect cell;

(3) the screening and the selection of the recombinant baculovirus clones expressing, separately or at the same time, the fibre(s), the penton base and possibly the hexon;

(4) the purification of the selected clones corresponding to replicable recombinant baculoviruses, containing one or more of the said genes, from at least one adenovirus and expressing the corresponding proteins;

(5) the extraction of the proteins expressed by the said recombinant baculoviruses, essentially comprising the lysis of insect cells, the elimination of cell and nuclear debris by centrifugation and the recovery of the supernatant; and (6) the purification of the dodecahedral protein complex according to the invention by application of the said supernatant (protein extract) to a sucrose gradient of which the range of concentrations varies as a function of the molecular weight and of the density of the dodecahedrons obtained and recovery of the fractions in the area of high sucrose concentrations; for example, for the complexes formed from Ad2 and/or Ad3, the sucrose gradient varies from 15 to 40%, and the fraction corresponding to a sucrose concentration of between 31 and 38% is recovered.

According to an advantageous embodiment of the said process, the insect cells of step (2) are selected in the group formed by the cells of *Spodoptera frugiperda* and the cells of *Trichoplusia ni*.

As a variant, the co-transfection of step (2) is employed in cells of *Spodoptera frugiperda* and the process comprises a second transfection step (4') of the purified clones of recombinant baculoviruses obtained in step (4) in *Trichoplusia ni* insect cells.

According to another advantageous embodiment of the said process, the baculovirus vector comprising a double, triple or multiple expression cassette according to step (1) is a vector comprising two or three strong promoters.

It is possible to mention, for example, the transfer vector pAcUW31 (Clontech®), which comprises (i) the polyhedrin promoter and the p10 promoter, the polyhedrin promoter being followed by a unique cloning site BamHI and polyhedrin polyadenylation signals, while the promoter p10 is followed by unique cloning sites BglII and EcoRI and by an SV40 polyadenylation signal, (ii) a replication origin M13, (iii) a replication origin pUC and (iv) a reporter gene, such as luciferase, β-galactosidase or resistance gene to an antibiotic (ampicillin, for example).

According to another advantageous embodiment of the said process, the said linearized baculovirus DNA fragment of step (2) is obtained from a vector containing three restriction sites Bsu36I and the gene lacZ in the place of the sequence coding for the polyhedrin, for example, the viral DNA vector BacPAK6® (Clontech), which vector is digested by the restriction enzyme Bsu36I before the said co-transfection of step (2).

According to another advantageous embodiment of the said process, the *Spodoptera frugiperda* insect cell of step (2) is selected from the group formed by the Sf21 cells and the Sf9 cells.

According to another advantageous embodiment of the said process, the purification of the clones of step (4) is carried out by employing at least two successive subclonings.

According to another advantageous embodiment of the said process, the *Trichoplusia ni* insect cells of step (5) are BTI-TN-5B1-4 cells (Invitrogen High Five®).

As a variant, the transfection of step (4') comprises the co-transfection of recombinant baculoviruses which contain the two genes (or the three genes in the case of an adenovirus containing two fibres per penton) from abovementioned adenoviruses, possibly combined with recombinant baculoviruses which contain only one of the two genes from adenoviruses.

According to the invention, the transfection can be carried out by different methods, according to the vector used: calcium phosphate method, DEAE-dextran method, stable transfer method, electroporation, liposome method.

According to another advantageous embodiment of the said process, step (5) of extraction of all of the proteins expressed by the recombinant baculovirus selected comprises the obtainment of a cell extract by lysis of the cells of *Trichoplusia ni*, at least several freezing-thawing cycles in a 10 mM Tris buffer pH 8, the elimination of the cell and nuclear debris present in the said cell extract by centrifugation for several minutes at 7000–10,000 g and the recovery of the supernatant.

According to yet another advantageous embodiment of the said process, step (6) of purification of the protein complex according to the invention comprises a centrifugation at 121,000 g at the top of the tube and at 275,000 g at the bottom of the tube for 17 to 19 hours and in the cold (40° C.).

According to yet another advantageous embodiment of the process, the dodecahedral protein complex purified in step (6) is subjected to concentration.

As a variant, step (2) comprises the isolation of the recombinant DNA (recombinant plasmid) obtained in a bacterium and the transfection of insect cells with the said recombinant DNA, according to the GIBCO-BRL process, called Bac-to-Bac® Baculovirus expression system.

The native dodecahedrons are advantageously obtained by extraction of the proteins expressed by cells infected by an adenovirus (see step (5) above) and purification of the dodecahedral complex on a sucrose gradient, under the same conditions as those stated above for the preparation of the recombinant dodecahedrons.

Besides the above measures, the invention additionally comprises other measures which will emerge from the description which follows, which refers to examples of carrying out the process to which the present invention relates as well as to the appended drawings, in which:

FIGS. 2A and 2B show the results obtained from cells expressing the fibre and the penton base from an Ad3 (Ad3 dodecahedron) and representing two SDS-PAGE electrophoresis gels obtained from sucrose gradient fractions: FIG. 2A: result of the transfer of protein (Western blot or immuno blot); FIG. 2B: result after staining with Coomassie Blue;

Figure 5:
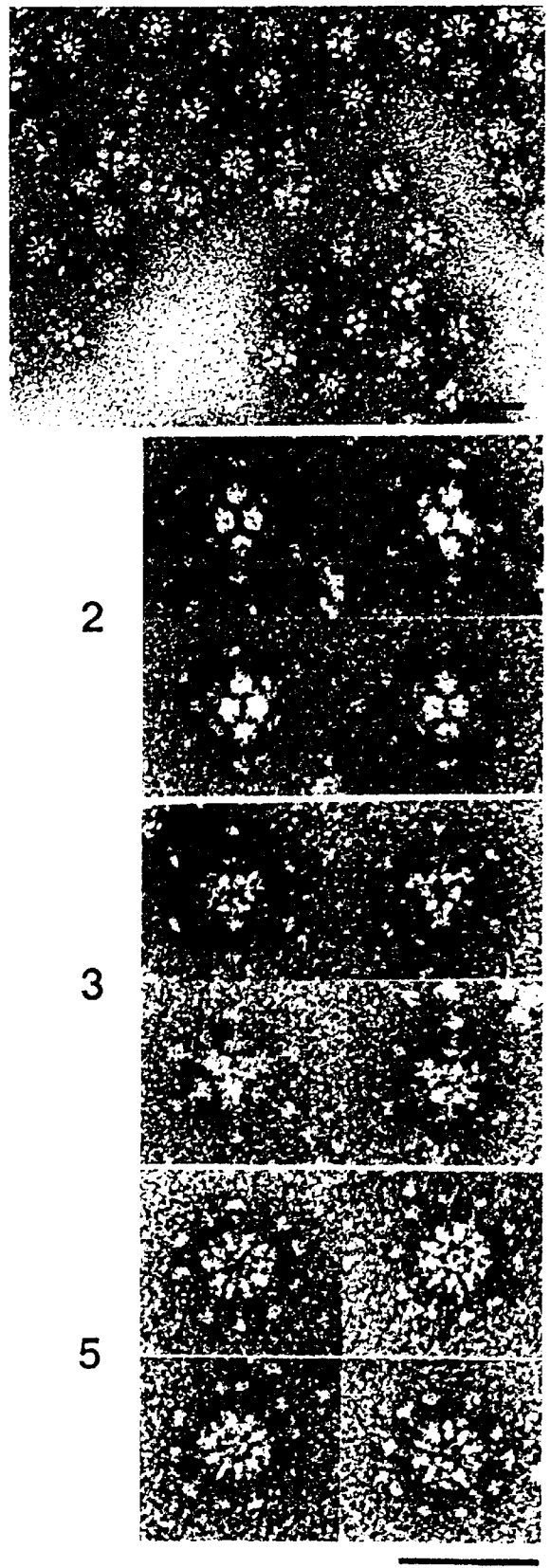
Figure 6:
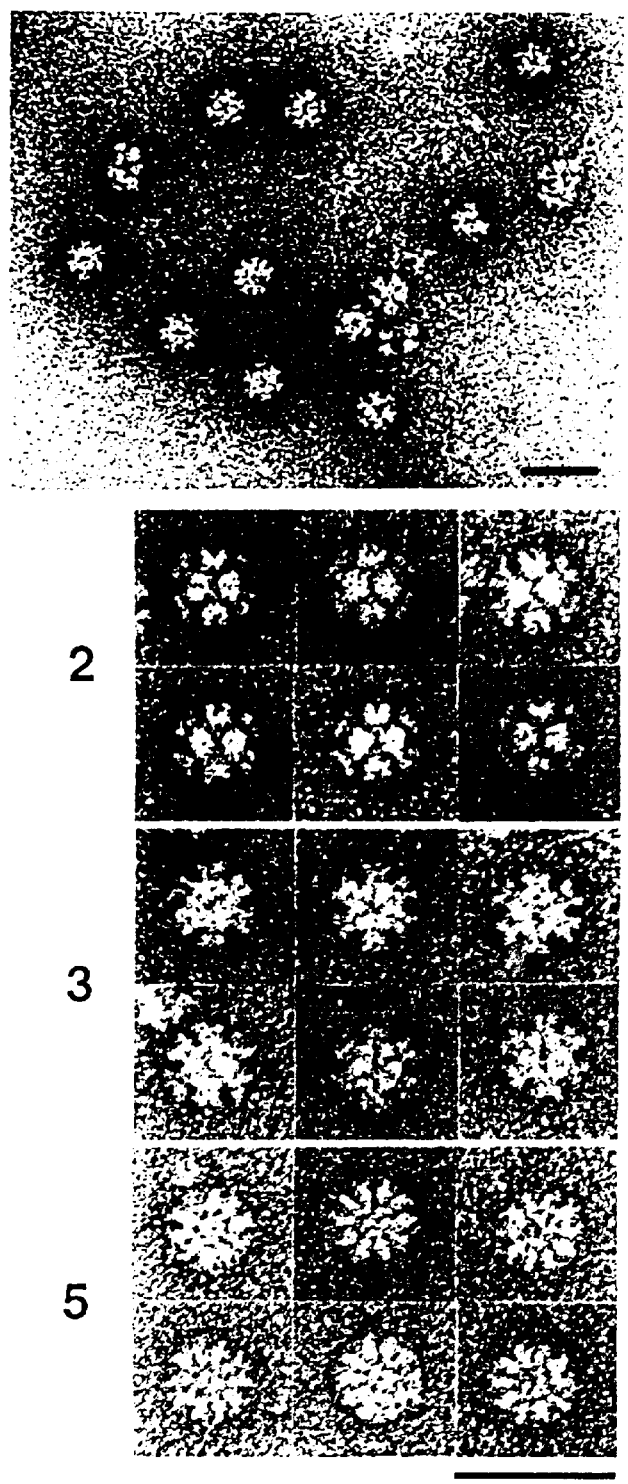
Figure 7:
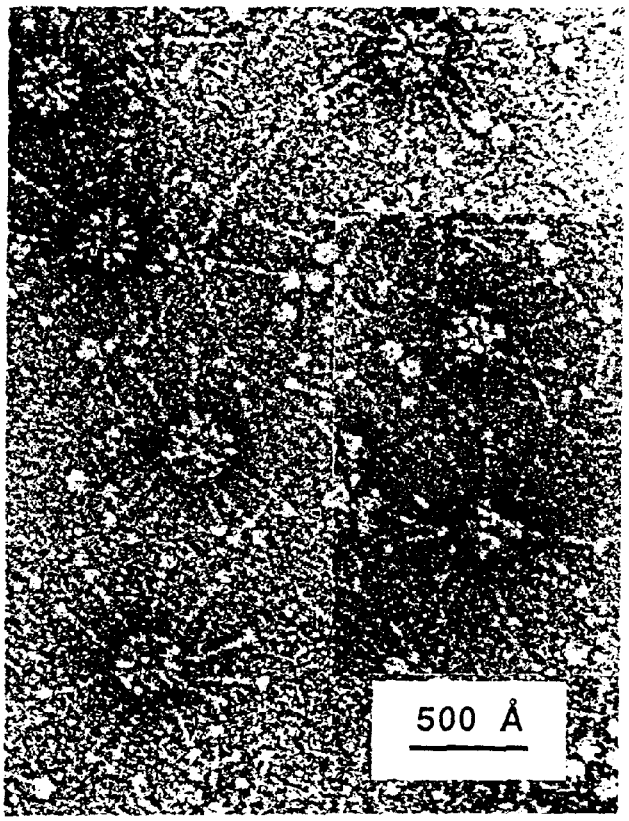
Figure 8:
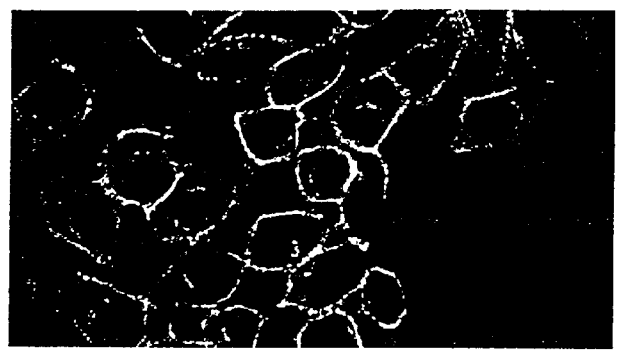
Figure 8:
Figure 8:
Figure 9:
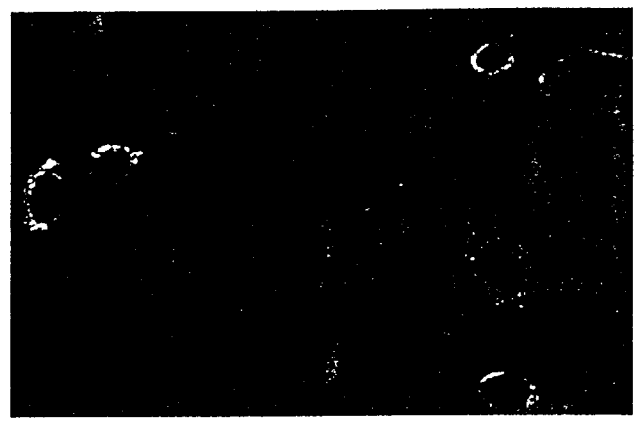
Figure 9:
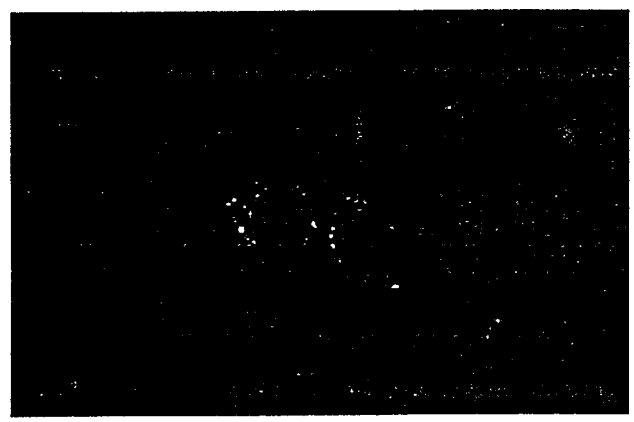
Figure 9:
Figure 10:
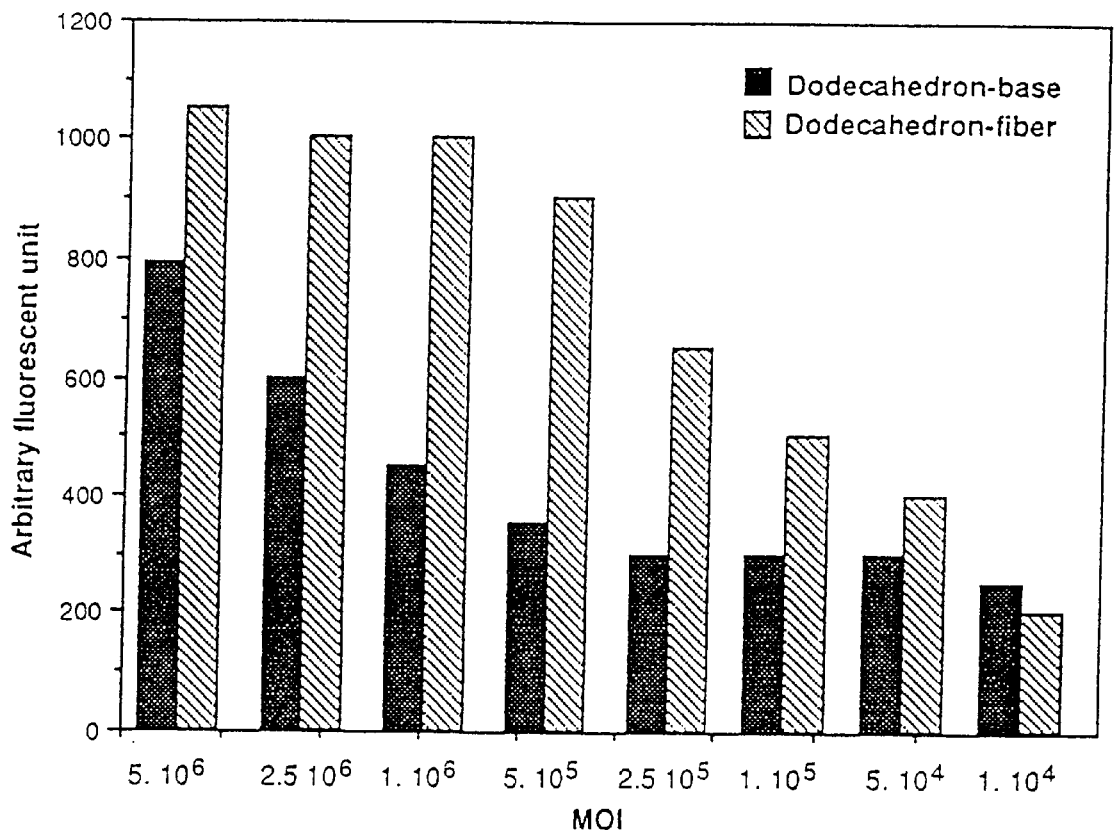
Figure 11:
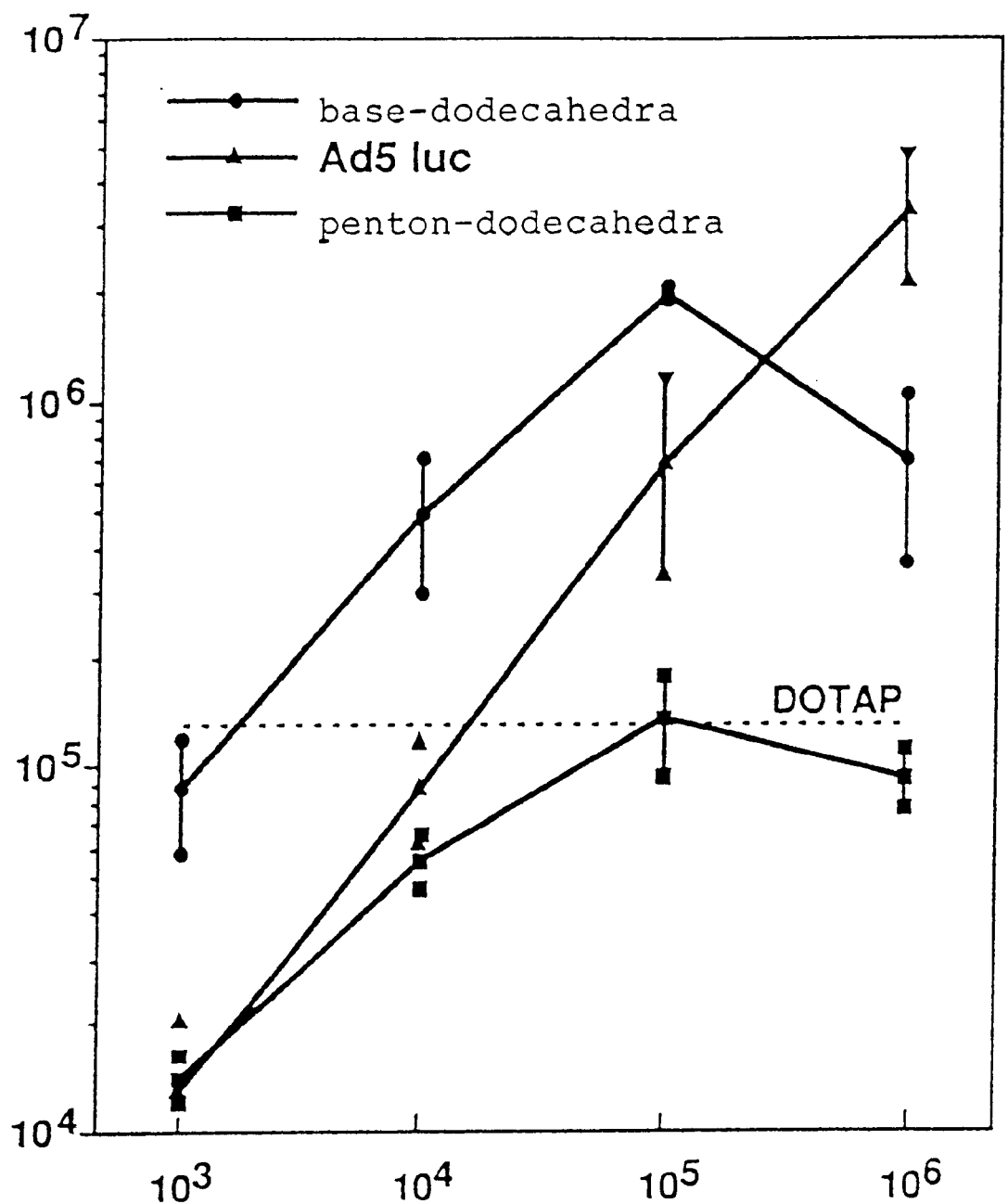
Figure 12:
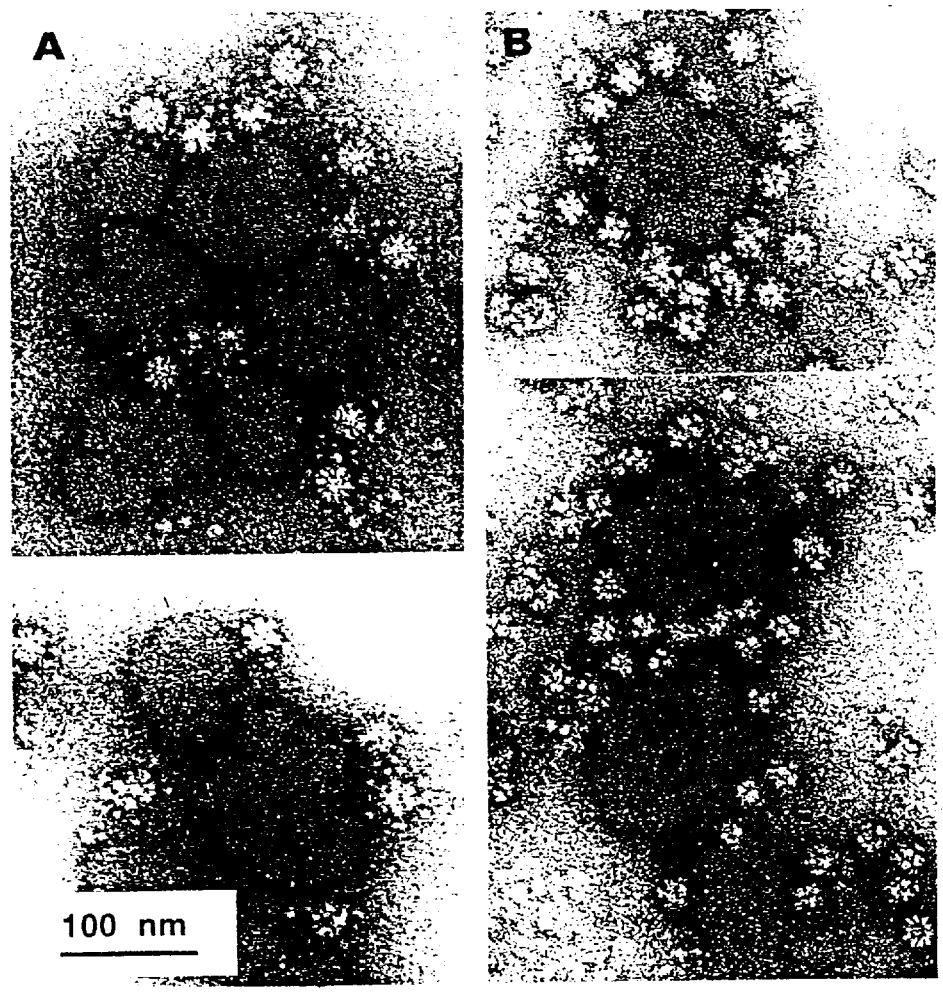
Figure 13:
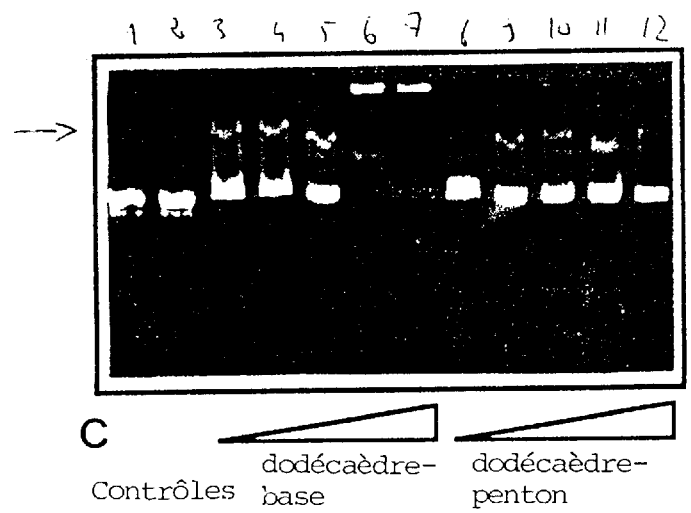

FIGS. 5 and 6 represent electron micrographs of dodecahedron-fibre and of dodecahedron-base of Ad3 respectively, negatively stained with 1% sodium silicotungstate; these micrographs are produced from a sample of material obtained after centrifugation of the sucrose gradient varying from 31 to 38%, mixed, dialysed and concentrated;

FIG. 7 represents a chimeric dodecahedron;

FIGS. 8 and 9 illustrate the internalization of the dodecahedral protein complex according to the invention into HeLa cells;

FIG. 10 illustrates the internalization of a dodecahedron-base and of a dodecahedron-fibre: the histograms □ illustrate the internalization of the dodecahedron-fibre and the histograms ■ illustrate the internalization of a dodecahedron-base; this figure comprises, on the abscissa, the quantity of viral/cell particles (=MOI or Multiplicity of Infection) and on the ordinate, the fluorescence units (arbitrary fluorescence units);

FIG. 11 illustrates the transfection of a plasmid containing the gene coding for luciferase in the presence of a dodecahedron-penton or of a dodecahedron-base, compared with the transfection effected by the recombinant adenovirus carrying the same gene; it shows, on the abscissa, the quantity of viral/cell particles (=MOI or Multiplicity of Infection) and on the ordinate, the relative quantity of light (=RLU or Relative Light Unit);

FIGS. 12A and 12B represent electro micrographs of DNA/peptide/dodecahedron-penton complexes (A) and of DNA/peptide/dodecahedron-base complexes (B) respectively, negatively stained with 1% sodium silicotungstate;

FIG. 13 shows the interaction of the bifunctional peptide with a dodecahedral protein complex according to the invention and a plasmid DNA; this figure represents an electrophoresis gel.

It must be well understood, however, that these examples are given solely by way of illustration of the subject of the invention, of which they do not in any manner form a limitation.

EXAMPLE 1

Cloning, Expression and Purification of the Adenovirus Dodecahedron of Type 3

1. Amplification by PCR of the genes of fibres and of the Penton base.

By using the PCR, it is possible to synthesize nucleotide sequences coding for useful polypeptides which can be inserted in an appropriate vector and used to transform a specific cell and to express them in the latter.

The method for producing the genes expressing the penton base and the adenovirus dodecahedron fibre according to the invention depends on the preselection of oligonucleotides as primers in a polymerization chain reaction (PCR).

The sequence of the genes of the penton base and of the fibre of the Ad3 has been described in CUZANGE et al., Gene, 1994, 146, 257–259 and SIGNAS et al., J. Virol., 1985, 53, 672–678 respectively.

The primers in 5' and in 3' used to amplify the gene coding for the penton base are 5'-GGATCCGATGAGGAGACGAGCC-3' (SEQ ID No. 1) and 5'-GGATCCTTAGAAAGTGCGGCTTG-3' (SEQ ID No. 2) respectively.

The 5' and 3' primers used to amplify the gene coding for the fibre are 5'-TTTCTT GAATTCCAGATGGCCAAGCGAGCT-3' (SEQ ID No. 3) and 5'-AAAAGGAATTCCAATAAAAAATGTTG-3' (SEQ ID No. 4) respectively.

The cloning sites are underlined and are BamHI, BamHI, EcoRI, EcoRI respectively. The ATG initiation codon is in bold and the TAA stop codon (or TTA in the complementary strand) is in italics.

The sequences of the fibres and penton bases of Ad2 and of Ad5 are especially described in Chroboczek J. et al., Virology, 1987, 161, 549–554 and Virology, 1992, 186, 280–285; Neumann R. et al., Gene, 1988, 69, 153–157.

The amplification by PCR is carried out on DNA extracts isolated from the virus, obtained by propagation in HeLa cells as described in HORWITZ ("Adenoviridae and their replication" in Virology, Fields and Knipe, eds. Raven Press, N.Y., 1990).

The PCR buffer contains, for example: KCl 50 mM, Tris HCl at pH 8.3 10 mM, $MgCl_2$ 1.5 mM, gelatin at 0.001%, ATP 200 μM, dTTP 200 μM, dCTP 200 μM, dGTP 200 μM and 2.5 units of DNA polymerase of Thermus acuaticus/100 μl of buffer. The PCR is carried out under the following conditions: after denaturation for 2 minutes at 94° C., the PCR comprises 25 cycles of 1 min at 94° C., 1 min at 55° C. and 1 min at 72° C.

2. Cloning of the PCR products in the pCR-Script™ intermediate vector

The poCR-Script™ cloning vector (Stratagene, catalogue No. 211190, 1994) has a high DNA ligation efficiency in the cloning of PCR products.

The PCR amplification products are fractionated by electrophoresis on 1% agarose gel in a TAE buffer; the suitable bands are separated and the DNA is extracted according to the GENECLEAN II™ procedure (Bio101, Inc.). The DNA fragments containing the genes coding for the penton base and the fibre are cloned, separately, in the abovementioned pCR-Script™ vector according to the directions of the supplier.

The clones are then treated to obtain the DNA, according to the procedure described in Sambrook et al. (*Molecular Cloning, a Laboratory Manual,* second edition) in the chapter concerning the minipreparations of plasmid DNA. Under these conditions, the presence of genes coding for the fibre and the penton base of the adenovirus is confirmed, by comparing the size of the fragments obtained after digestion by BamHI and EcoRI with standard products on agarose gel.

The positive clones are amplified, the plasmid DNA is isolated and the genes of the fibre and of the penton base are obtained after digestion with the same restriction enzymes (BamHI and EcoRI), according to the methods of genetic engineering usually used in molecular cloning (Sambrook et al., mentioned above).

3. Cloning of genes of fibres and of penton base in an expression vector.

The double-expression vector pAcUW31® (Clontech) is used to express the dodecahedron.

Firstly, the gene of the penton base is introduced at the level of the BamHI site of this vector, upstream of the polyhedrin promoter. The cloning is verified by hybridization with a non-radioactive probe corresponding to the penton base containing dUTP linked to fluorescein according to the procedure of the ECL® kit. The orientation of the insert with respect to the promoter is determined in the positive clones by a restriction analysis.

In a second step, the gene coding for the fibre is inserted at the level of the EcoRI site of the said vector, downstream of the promoter of the p10 gene. The cloning and the orientation of the insert are verified as stated above.

The sequence of the gene coding for the base and of the gene coding for the fibre are verified in the resultant plasmid. No mutation is detected. Similarly, the vectors which only carry either the gene coding for the fibre, or the gene coding for the penton base are prepared and analysed as described above.

The expression plasmids which carry either the two genes, or one of the two genes of interest, are transformed in a TG-1 *E. coli* strain, as described in HANAHAN (J. Mol. Biol., 1983, 166, 557–580) and a large-scale purification of the plasmid is carried out by using the well-known techniques of genetic engineering (Sambrook et al., mentioned above).

It is likewise possible, if necessary (in the case of the use of adenoviruses comprising two fibres), to employ a triple-expression vector, such as described in A. J. Belyaev and T. Roy (N.A.R., 1993, 21, 1219–1223).

4. Transfection in insect cells.

The recombinant plasmids (100 ng) are (separately) cotransfected with a linearized baculovirus (Clontech: Bac-PAK6® viral DNA digested by the enzyme Bsu36I) in the presence of lipofectine® (GIBCO) in *Spodoptera frugiperda* cells (Sf21) and *Trichoplusia ni* cells (High-Five®) according to the technique described by KITTS et al. (N.A.R., 1990, 18, 19, 5667–5672). This method allows a transformation efficiency of greater than 80% to be obtained. A few clones are chosen in each case and the expression is detected by the Western blot technique, carried out with fibre antigen-specific polyclonal rabbit antibodies and penton bases.

5. Purification of the positive clones.

The isolates of recombinant baculoviruses are plated out 3 times, followed by a titration according to the method of KING and POSSEE (The baculovirus expression system, A laboratory guide, L. A. KING and R. D. POSSEE, ed.: CHAPMAN & HALL, 1992). The expression of the two proteins is followed by the Western blot technique such as stated above.

6. Purification of the protein.

The kinetics of the dodecahedron expression is followed in the two cell types for 5 days, on adherent cells, cultured at 27° C. in GIBCO TC 100 medium containing 5% of foetal calf serum (Sf21 or Sf9 cells) or on GIBCO TC 100 medium containing 10% foetal calf serum (High-Five® cells). Inasmuch as the protein expression yield is significantly greater in the High-Five® cells, protein expression on a large scale can be carried out only in these cells.

Tests to increase the rate of expression by cotransfection in insect cells with a baculovirus carrying the two genes and different quantities of baculovirus only carrying a single gene were not significant. 3 days after the infection with the recombinant baculovirus (multiplicity of infection 5), High-Five® cells are harvested in a 10 mM Tris buffer, pH 8, containing protease inhibitors.

Cell lysis is carried out by employing 3 freezing-thawing cycles in the same Tris buffer. The lysis extract is freed from solid elements (cell and nuclear debris) by centrifugation for 5 min at 7000–10,000 g, then is subjected to a sucrose gradient varying from 15 to 40% (11 ml) in a gradient buffer comprising 10% glycerol, 150 mM NaCl, 10 mM Tris-HCl, pH 7.4 and 2 mM EDTA.

After centrifugation at 4° C. for 18 hours in a Beckman SW 41 rotor at 121,000 g at the top of the tube and at 275,000 g at the bottom of the tube; the sample treated in this way is recovered through the top, in 800 μl fractions.

Under these conditions, the dodecahedron is recovered in the fractions containing 31–38% of sucrose. These fractions are mixed and dialysed against a gradient buffer without sucrose and glycerol.

The dodecahedron is concentrated by centrifugation on Centriprep® (Amicon).

FIGS. 2A and 2B illustrate the results obtained after purification of the dodecahedron: they are obtained from aliquots of each fraction, obtained from the sucrose gradient as described above, denatured by heat in the presence of 1% SDS and electrophoresis in two 10% SDS-polyacrylamide gels; the proteins are analysed on one of the gels by transfer of proteins, followed by a reaction with anti-fibre and anti-penton base-specific antibodies (Western blot) (FIG. 2A) and on the second gel by Brilliant Coomassie Blue staining. The fractions situated at the top of the tube contain the penton bases and free fibres and the fractions recovered in the 31–38% of sucrose zone contain the dodecahedral protein complex according to the invention.

FIG. 5 represents an electron micrograph of negatively stained Ad3 dodecahedron-fibre; the upper figure illustrates a field containing a certain number of dodecahedrons in different orientations, while the figures numbered 2, 3 and 5 illustrate dodecahedrons on a film-support according to their different axes of symmetry (of order 2, of order 3 and of order 5, respectively); in the figure illustrating the axis of symmetry of order 5, 10 fibres are visible, while the 11th and 12th fibres are probably in the vertical plane with respect to the plane of the paper.

FIG. 6 represents an electron micrograph of negatively stained Ad3 dodecahedron-base; the upper figure illustrates a field containing a certain number of dodecahedrons in different orientations, while the figures numbered 2, 3 and 5 illustrate dodecahedrons on a film-support according to their different axes of symmetry (of order 2, of order 3 and of order 5, respectively).

These fractions contain spherical particles consisting of pentons (FIG. 5), combined in a dodecahedron, through the intermediary of their bases.

In FIGS. 5 and 6, the different axes of symmetry of order 2, of order 3 and of order 5 are easily locatable.

The diameter of the dodecahedron with the fibres (between the opposed heads of 2 fibres) is 49 nm, while the diameter of the base part (from the upper part of one base to the upper part of the opposite base) is 27.8 nm (diameter almost identical to the diameter of the dodecahedron without fibre (27.5 nm)). The pentons of the dissociated dodecahofedrons which can be found have a size of 21.4±1 nm (n=24), measured from the lower part of the base to the end of the fibre head.

The interior of the dodecahedron is formed of a cavity having an internal volume of approximately 350 $nm^3$.

7. Role of the Penton base in the formation of the dodecahedron.

The dodecahedrons formed from penton bases and fibres can be formed in insect cells, not only through the process of co-expression from a baculovirus carrying two genes, but likewise from a co-infection with two baculoviruses, each of these carrying a gene (FIGS. 3A, B).

It is this approach which has been chosen to study the role of the penton base in the formation of the dodecahedron.

When an Ad2 base is used with an Ad2 fibre or an Ad3 fibre, the proteins obtained in the high-density sucrose fractions contain non-structured aggregates of pentons (FIG. 4D) or of bases (FIG. 4E).

Chimeric adenovirus pentons can be formed in vitro, by incubation of purified fibres and of penton bases derived from different serotypes.

Figure 4:
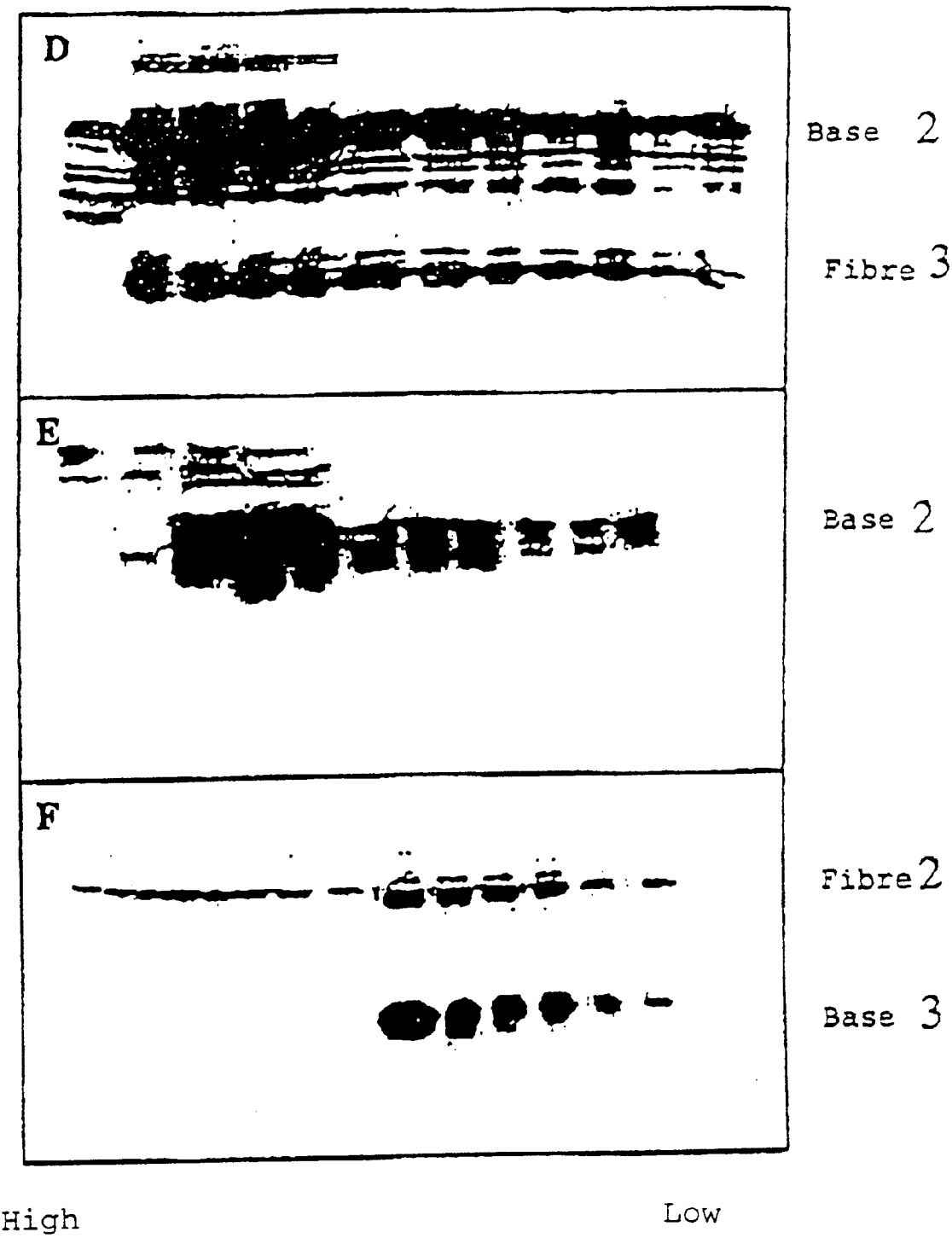

Using such a method, dodecahedrons consisting uniquely of bases have been obtained. After incubation of a dodecahedron made only of Ad3 bases with native Ad2 fibres, isolated from cells infected with Ad2, dodecahedrons carrying the inserted heterologous fibres are obtained (FIGS. 4 and 7).

These experiments show that as far as the study of the Ad2 and Ad3 adenoviruses is concerned, the formation of a dodecahedron depends on the presence of the Ad3 base and not of the Ad2 base.

When the Ad3 penton base is expressed only in the baculovirus system, it is recovered virtually exclusively in the dodecahedral form (FIG. 3C).

Chimeric dodecahedron formation, when Ad2 fibres are inserted into a preformed dodecahedron base, confirms the above results relating to the formation of chimeric pentons.

Figure 1:
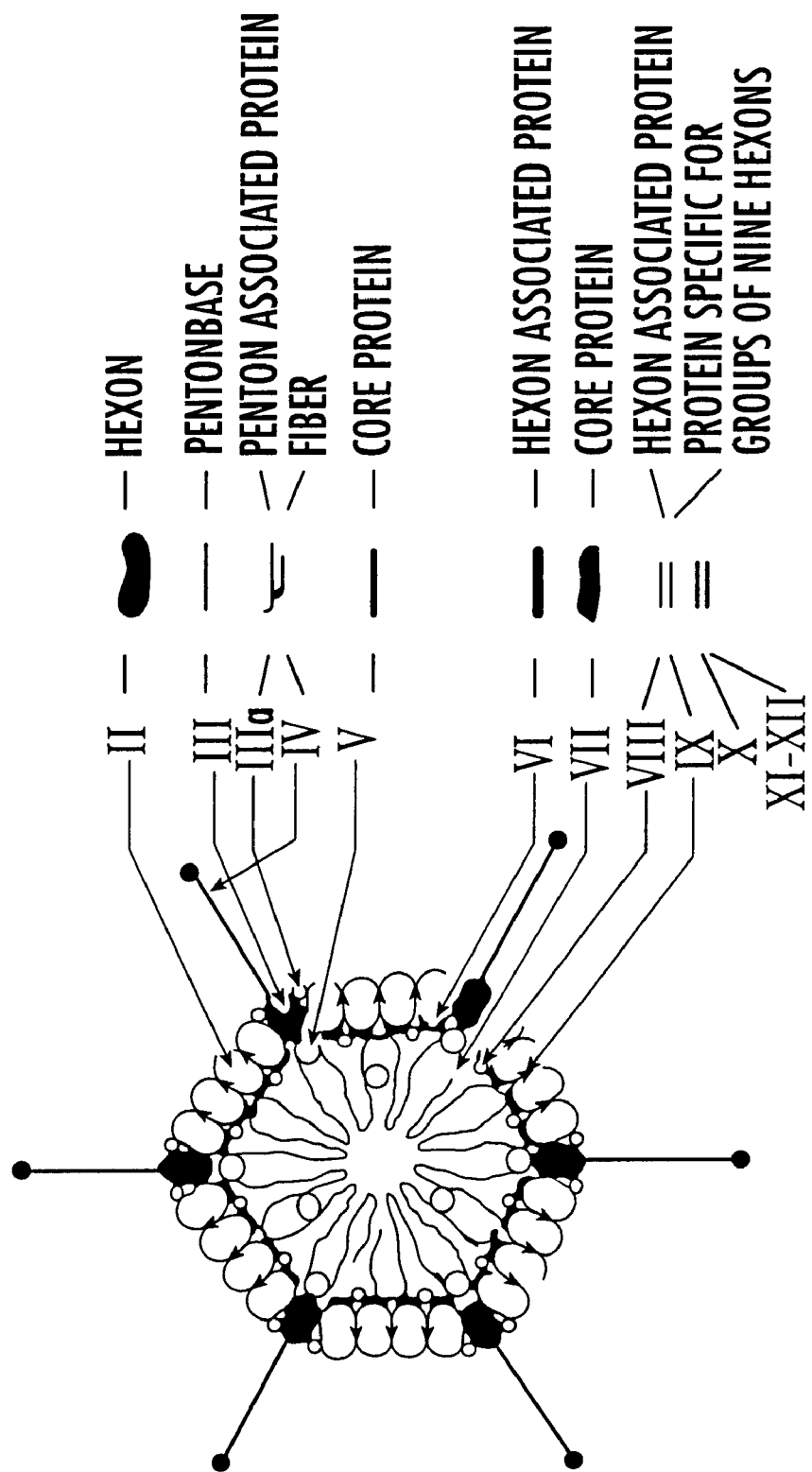
FIG. 1 represents a schematic view of an adenovirus.
Figure 3:
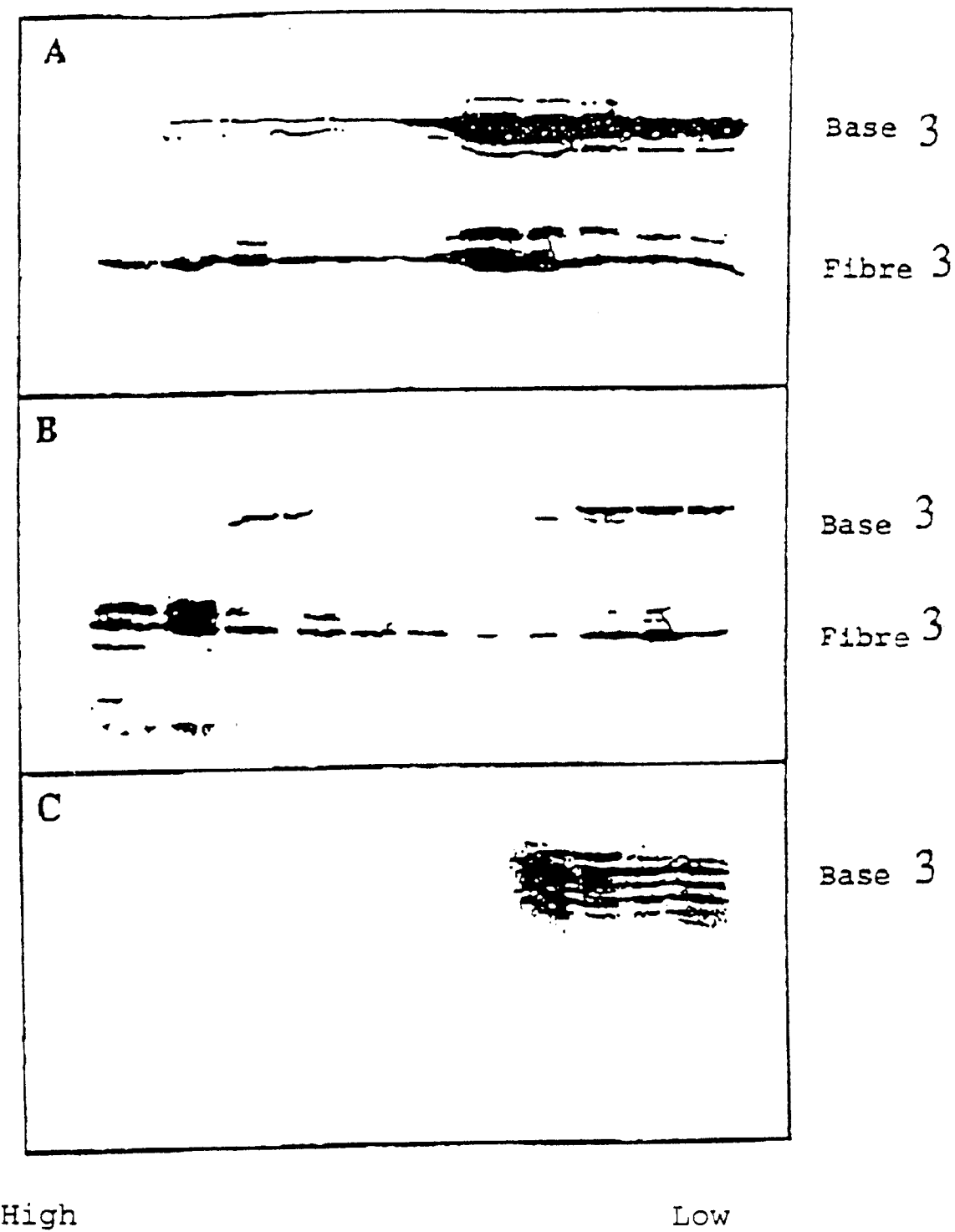
FIGS. 3 and 4 illustrate the role of the penton base in the formation of the dodecahedron.

FIGS. 3 and 4 illustrate the role of the penton base in the formation of the dodecahedron. The Western blot analysis of the different fractions of the sucrose density gradient is carried out as illustrated in Example 1: FIG. 3A: co-expression of the Ad3 base and fibre from a baculovirus; FIG. 3B: co-expression of the Ad3 base and fibre from a coinfection with two baculoviruses, each carrying one of the genes; FIG. 3C: expression of the Ad3 base; FIG. 4D: expression of the Ad2 base and the Ad3 fibre from a coinfection with two baculoviruses each carrying one gene; FIG. 4E: expression of the Ad2 base; FIG. 4F: in vitro formation of a dodecahedron by incubation of a dodecahedron-base (Ad3) preformed in vivo with native Ad2 fibres.

EXAMPLE 2

Intracellular Accumulation of Dodecahedrons

FIGS. 8 and 9 are photographs which illustrate the internalization of the dodecahedron in the HeLa cells.

To produce these photographs, portions of $5\times10^4$ HeLa cells are cultured in a DMEM medium containing 10% foetal calf serum on cover glasses (diameter: 1.2 cm). Each cover glass is incubated for 2 hours at 4° C. with 1 µg of dodecahedron in 50 µl of 3% PBS-BSA. The cells are washed twice with cold PBS and incubated at 37° C. in 3% PBS-BSA for 0 to 45 min. The cells are fixed and permeabilized by a treatment with methanol for 5 min at −20° C. The cover glasses are then incubated for 1 hour at 37° C. with an anti-fibre antibody (1:200, 50 µl in 3% PBS-BSA/ cover glass), washed twice with PBS, then incubated for 30 min with an antibody conjugated to fluorescein (1:250, 50 µl in 3% PBS-BSA/cover glass). After a last wash in PBS, the cover glasses are mounted on a microscope slide with a drop of 50 mg/ml 1,4-diazabicyclo[2.2.2.]octane (Sigma) in 50% glycerol/50% PBS. The observations are carried out on an MRC600 confocal microscope (Bio-Rad).

FIGS. 8 and 9 show that after incubation at 4° C., there is only attachment of the dodecahedral protein complex to the said cells, while at 37° C. there is internalization of the said complex.

At 4° C., the dodecahedron is at the surface of the cells (visible after staining with an anti-fibre antibody); when the HeLa cells are transferred at 37° C., FIGS. 8 and 9 illustrate the progress of the internalization of the dodecahedron as a function of time: up to 5 minutes, the image is very similar (no internalization); after incubation for 10–15 minutes (FIG. 8), a massive transfer of the dodecahedron in the vicinity of the nuclear membrane is observed. A longer incubation (20–45 minutes, FIG. 9) shows a more diffuse signal, which illustrates the cytoplasmic evacuation of the dodecahedron. Similar results are obtained when the progress of the dodecahedron is followed with an antibase serum.

A similar experiment is carried out with a dodecahedron only formed of Ad3 bases. No attachment or internalization is observed by confocal electron microscopy when a molar ratio is used comparable to that used in the preceding experiment. However, when larger quantities of dodecahedron-base are used, internalization is observed. Quantities of dodecahedron-base 10 to 20 times larger are necessary to obtain a degree of internalization equivalent to that obtained with the dodecahedron-fibre. FIG. 10 illustrates the results obtained after internalization for one hour. Similar results are obtained after internalization for 30 minutes.

These experiments show that the absence of fibre can be compensated by larger quantities of dodecahedron-base; however, the presence of fibre confers on the dodecahedron a higher efficacy at the time of entering of the cells.

These results can be explained inasmuch as for the adenovirus of serotype 2 (Ad2), the binding affinity of the fibre is 30 times higher than that of the penton base ($K_d$s of 1.7 and 55 nM, respectively).

At the temperature at which the attachment and the internalization of the virus takes place, it has been shown that the Ad3 dodecahedron attaches to the HeLa cells and that after 10 to 20 minutes, at the temperature suited to the entry of the virus, the dodecahedron is found in the cytoplasm, targeted at the cytoplasmic surface of the nuclear membrane. The overall kinetics seem to be similar to those of the first steps of a viral infection, when 20 minutes after attachment approximately 50% of the entering viral inoculum (Ad5) is at the periphery of the nucleus.

In the case of the cellular entry of the Ad3 dodecahedron, the integrity of the dodecahedron and of its components is not compromised either during the first 20 minutes or later (FIGS. 8 and 9).

EXAMPLE 3

Transfection of Human Cells with the Luciferase Gene Utilizing the Ad3 Dodecahedron with or without Fibre and a Bifunctional Peptide: Comparison of the Efficacy of Transfection of an Adenoviral Protein Complex According to the Invention, with Respect to a Recombinant Adenovirus or Liposomes (DOTAP)

Preparation of the peptide

The bifunctional peptide synthesized has 20 amino acids corresponding to the N-terminal part of the Ad3 fibre and 20 lysines of the C-terminal side, which will give a polycation which is able to immobilize polyanions such as DNA. Polypeptide sequence I: AKRARLSTSFNPVYPYEDES(K)$_{20}$ (SEQ ID No. 5).

Other bifunctional peptides can be constructed: they have, for example, the N-terminal end of any adenovirus fibre and extend towards their C-terminal end either by (1) a polyarginine or (2) a part or a complete core protein sequence of any adenovirus, such as VII protein, µ protein of human adenoviruses, or homologous core proteins found in the adenoviruses of other animals.

The 4 following peptides have likewise been synthesized:

polypeptide II (50 amino acids): AKRARLSTSFNPVYPYEDESSRRRRRSRPTTVSNRL-VVVSTRRRSSRRRR (SEQ ID No. 6)

polypeptide III (42 amino acids): SFNPVYPYEDESSRRRRRSRPTTVSNRLVVVSTRRR-SSRRRR (SEQ ID No. 7)

polypeptide IV: SFNPVYPYEDESMRRAHHRRRRASHR (SEQ ID No. 8)

polypeptide V: <u>SFNPVYPYEDES</u>GRRRKRTATRRRS (SEQ ID No. 9)

In polypeptides II and III, the C-terminal fragment, in bold, of 30 amino acids corresponds to the complete sequence of the VII protein of the avian adenovirus serotype 1 (FAV1 or CELO) and the underlined part corresponds to a longer or shorter fragment of the Ad3 fibre.

In the polypeptides IV and V, the C-terminal part, in bold, corresponds respectively to the µ protein of the human adenovirus and to the µ protein of the avian CELO Ad1.

All these bifunctional peptides can be used for the transfection of DNA, separately or as a mixture.

Preparation of the plasmid containing the DNA to be transported (active substance)

The plasmid coding for the luciferase reporter gene (pGL3-control vector) (Promega) is produced in *E. coli* JM109 and purified by Qiagen.

Method

Mixture 1: dodecahedron samples without or with fibre are incubated in a DMEM medium with 5 µg of bifunctional peptide for 15 minutes, at ambient temperature, and then 1.5 µg of pGL3 plasmid carrying the luciferase gene are added.

Mixture 2: in addition, a mixture of DOTAP (Boehringer) and of 1.5 µg of pGL3 plasmid is prepared, as stated by the supplier, with a DOTAP/DNA ratio of 4.

Portions of $10^5$ HeLa cells/well, in a plate comprising 24 wells, are transfected in parallel with the mixtures above and with the Ad5luc recombinant adenovirus for one hour at 37° C.

The emission of light is measured in cell lysates, 48 hours afterwards, with the aid of the Promega kit.

FIG. 11 illustrates the results obtained.

EXAMPLE 4

Demonstration of the Interaction of the Bifunctional Peptide with the Adenoviral Protein Complex according to the Invention and the Plasmid DNA to be Transported DNA/peptide/dodecahedron-penton and DNA/peptide/dodecahedron-base complexes are prepared as stated in the transfection tests (see Example 3) without addition of medium; the electron micrographs of these complexes are illustrated in FIGS. 12A and 12B and show the DNA in a compact form with the dodecahedron-penton (A) and the dodecahedron-base (B). In parallel, increasing quantities of dodecahedron-base are incubated with 200 µg of peptide for 15 minutes at ambient temperature; 250 ng of plasmid DNA are added, then 5 minutes later the samples are deposited on a 1% agarose gel prepared in TBE buffer, and are then subjected to electrophoresis for 1 hour at 50 volts.

The DNA is revealed by staining with ethidium bromide, followed by UV visualization. All the samples contain plasmid DNA. Track 1 corresponds to plasmid DNA alone; track 2 corresponds to plasmid DNA mixed with the dodecahedron-base (no peptide); tracks 3 to 7 comprise plasmid DNA, the bifunctional peptide and 1, 10, 100, 500 and 1000 ng of dodecahedron-base respectively; tracks 8 to 12 comprise plasmid DNA, the bifunctional peptide and 1, 10, 100, 500 and 1000 ng of dodecahedron-penton respectively.

This figure shows well that the peptide attaches to the dodecahedron and to the plasmid and modifies the structure: the plasmid DNA becomes compact and migration is retarded: presence of an intermediate band (see arrow) or even absence of migration (see tracks 6 and 7).

As is evident from what has gone before, the invention is by no means limited to those of its embodiments, its methods of being carried out and application which have just been described in a more explicit fashion; on the contrary, it embraces all the variants thereof which can occur to the technician skilled in the subject, without deviating from the context or the scope of the present invention.

What is claimed is:

1. A proteinaceous vector for delivering a chemical substance into an animal cell, comprising an adenoviral protein complex having a dodecahedral structure consisting of 12 adenoviral penton bases or 12 adenoviral pentons each consisting of a penton base and a fiber.

2. The proteinaceous vector of claim 1, wherein said dodecahedral structure formed from 12 adenoviral penton bases has a molecular weight of between $3.2 \times 10^6$ Daltons and $4 \times 10^6$.

3. The proteinaceous vector of claim 1, wherein said dodecahedral structure formed from 12 adenoviral pentons has a molecular weight of between $4.8 \times 10^6$ Daltons and $6.6 \times 10^6$ Dalton.

4. The proteinaceous vector of claim 1, wherein said 12 adenoviral pentons are bound together by said penton bases in said pentons.

5. The proteinaceous vector of claim 1, wherein said dodecahedral structure has an interior cavity.

6. The proteinaccous vector of claim 1, wherein said protein complex is proteolytically stable.

7. The proteinaceous vector of claim 1, wherein said penton base and fiber are derived from at least one adenovirus selected from the group consisting of Ad2, Ad3, Ad4, Ad5, Ad7, Ad9, Ad11, Ad15, Ad40, Ad41 adenovirus, and avian adenoviruses.

8. The proteinaceous vector of claim 1, wherein said penton base and fiber are derived from at least one adenovirus selected from the group consisting of Ad3, Ad4, Ad7, Ad9, Ad11, and Ad15 adenovirus.

9. The proteinaceous vector of claim 1, wherein said penton bases in said pentons are derived from Ad3 adenovirus, and said fibers are derived from Ad2 or Ad5 adenovirus.

10. The proteinaceous vector of claim 1, wherein at least one of said bases or said fibers is in a modified form.

11. A composition comprising a proteinaceous vector in accordance with claim 1 and a chemical substance bound to said vector.

12. The composition of claim 11, wherein said chemical substance is selected from the group consisting of nucleic acid sequences, proteins, peptides, ribozymes, and pharmaceutically active agents.

13. The composition of claim 11, wherein said chemical substance is a nucleic acid sequence.

14. The composition of claim 11, wherein said composition further comprises a ligand for binding said chemical substance to said proteinaceous vector.

15. The composition of claim 14, wherein said ligand is a bifunctional peptide comprising a first amino acid sequence and a second amino acid sequence.

16. The composition of claim 14, wherein said chemical substance is a nucleic acid sequence, and said ligand comprises an N-terminus having an N-terminal amino acid sequence of an adenoviral fiber, and a C-terminus comprising a sequence selected from the group consisting of polyarginine, poly-L-lysine, cysteine, transferrin/poly-L-lysine complex, and an adenoviral core protein sequence.

17. A method for introducing a chemical substance into an animal cell, comprising:
providing a composition comprising said chemical substance bound to a proteinaceous vector, said vector comprising an adenoviral protein complex having a dodecahedral structure formed from 12 adenoviral penton bases or 12 adenoviral pentons each consisting of a penton base and a fiber; and
contacting said composition to said animal cell under conditions suitable for internalization by said cell.

18. The method of claim 17, wherein said chemical substance is selected from the group consisting of nucleic acid sequences, proteins, peptides, and pharmacologically active chemical substances.

19. The method of claim 17, wherein said chemical substance is a nucleic acid sequence comprising a coding sequence for a protein or peptide and a promoter for transcription of said coding sequence in said animal cell.

20. The method of claim 17, wherein said composition further comprises a ligand for binding said chemical substance to said proteinaceous vector.

21. The method of claim 17, wherein said ligand is a bifunctional peptide comprising a first amino acid sequence and a second amino acid sequence.

22. The method of claim 20, wherein said chemical substance is a nucleic acid sequence, and said ligand comprises an N-terminus having an N-terminal amino acid sequence of an adenoviral fiber, and a C-terminus comprising a sequence selected from the group consisting of polyarginine, poly-L-lysine, cysteine, transferrin/poly-L-lysine complex, and an adenoviral core protein sequence.

23. The method of claim 20, wherein said animal cell expresses an integrin receptor and said animal cell is selected from the group consisting of epithelial cells, endothelial cells, blood platelets, lymphoid cells, and cancerous cells.

24. A process for preparing an adenoviral protein complex, comprising:
providing a recombinant baculovirus capable of expressing an adenoviral penton base;
multiplying said recombinant baculovirus in an insect cell selected from the group consisting of *Spodoptera frugiperda* cells and *Trichoplusia ni* cells;
preparing a protein extract containing said adenoviral penton base;
centrifuging said protein extract in a sucrose gradient; and
isolating said adenoviral protein complex from the gradient, wherein said adenoviral protein complex has a dodecahedral structure formed from 12 adenoviral penton bases.

25. The process of claim 24, further comprising:
providing a recombinant baculovirus capable of expressing an adenoviral fiber;
multiplying said recombinant baculovirus expressing an adenoviral fiber in an insect cell selected from the group consisting of *Spodoptera frugiperda* cells and *Trichoplusia ni* cells,
wherein said protein extract also contains said adenoviral fiber, and wherein said adenoviral protein complex has a dodecahedral structure formed from 12 adenoviral pentons each consisting of an adenoviral penton base and an adenoviral fiber.

26. The process of claim 24, wherein said sucrose gradient has a sucrose concentration range of from about 15% to about 40%.

27. The process of claim 24, wherein said *Spodoptera frugiperda* cell is an Sf9 cell or an Sf21 cell.

* * * * *

UNITED STATES PATENT AND TRADEMARK OFFICE
CERTIFICATE OF CORRECTION

PATENT NO. : 6,083,720
DATED : July 4, 2000
INVENTOR(S) : Chroboczek et al.

It is certified that error appears in the above-identified patent and that said Letters Patent is hereby corrected as shown below:

Column 7, lines 40-41, "(40°C.)" should read --(4°C.)--.

Column 9, line 24, "poCR-Script™" should read --pCR-Script™--.

Column 10, line 47, begin new paragraph with "3 days....".

Column 13, line 56, after "polypeptide" close up space.

Column 17, line 67, after "4x10$^6$" insert --Daltons--.

Column 18, line 60, "Dalton" should read --Daltons--; line 66, "proteinaccous" should read --proteinaceous--.

Signed and Sealed this

Tenth Day of April, 2001

*Attest:*

NICHOLAS P. GODICI

*Attesting Officer*    Acting Director of the United States Patent and Trademark Office

SEQUENCE LISTING

<160> NUMBER OF SEQ ID NOS: 9

<210> SEQ ID NO 1
<211> LENGTH: 22
<212> TYPE: DNA
<213> ORGANISM: Artificial Sequence
<220> FEATURE:
<223> OTHER INFORMATION: nucleotide primer

<400> SEQUENCE: 1
ggatccgatg aggagacgag cc                                    22

<210> SEQ ID NO 2
<211> LENGTH: 23
<212> TYPE: DNA
<213> ORGANISM: Artificial Sequence
<220> FEATURE:
<223> OTHER INFORMATION: nucleotide primer

<400> SEQUENCE: 2
ggatccttag aaagtgcggc ttg                                   23

<210> SEQ ID NO 3
<211> LENGTH: 30
<212> TYPE: DNA
<213> ORGANISM: Artificial Sequence
<220> FEATURE:
<223> OTHER INFORMATION: nucleotide primer

<400> SEQUENCE: 3
tttcttgaat tccagatggc caagcgagct                            30

<210> SEQ ID NO 4
<211> LENGTH: 26
<212> TYPE: DNA
<213> ORGANISM: Artificial Sequence
<220> FEATURE:
<223> OTHER INFORMATION: nucleotide primer

<400> SEQUENCE: 4
aaaaggaatt ccaataaaaa atgttg                                26

<210> SEQ ID NO 5
<211> LENGTH: 40
<212> TYPE: PRT
<213> ORGANISM: Artificial Sequence
<220> FEATURE:
<223> OTHER INFORMATION: hybrid peptide

<400> SEQUENCE: 5

Ala Lys Arg Ala Arg Leu Ser Thr Ser Phe Asn Pro Val Tyr Pro Tyr
 1               5                  10                  15

Glu Asp Glu Ser Lys Lys Lys Lys Lys Lys Lys Lys Lys Lys
             20                  25                  30

Lys Lys Lys Lys Lys Lys Lys Lys
             35                  40

<210> SEQ ID NO 6
<211> LENGTH: 50
<212> TYPE: PRT
<213> ORGANISM: Artificial Sequence
<220> FEATURE:
<223> OTHER INFORMATION: hybrid peptide -continued

```
<400> SEQUENCE: 6

Ala Lys Arg Ala Arg Leu Ser Thr Ser Phe Asn Pro Val Tyr Pro Tyr
1               5                   10                  15

Glu Asp Glu Ser Ser Arg Arg Arg Arg Ser Arg Pro Thr Thr Val
            20                  25                  30

Ser Asn Arg Leu Val Val Ser Thr Arg Arg Arg Ser Ser Arg Arg
            35                  40                  45

Arg Arg
    50

<210> SEQ ID NO 7
<211> LENGTH: 42
<212> TYPE: PRT
<213> ORGANISM: Artificial Sequence
<220> FEATURE:
<223> OTHER INFORMATION: hybrid peptide

<400> SEQUENCE: 7

Ser Phe Asn Pro Val Tyr Pro Tyr Glu Asp Glu Ser Ser Arg Arg Arg
1               5                   10                  15

Arg Arg Ser Arg Pro Thr Thr Val Ser Asn Arg Leu Val Val Val Ser
            20                  25                  30

Thr Arg Arg Arg Ser Ser Arg Arg Arg
            35                  40

<210> SEQ ID NO 8
<211> LENGTH: 26
<212> TYPE: PRT
<213> ORGANISM: Artificial Sequence
<220> FEATURE:
<223> OTHER INFORMATION: hybrid peptide

<400> SEQUENCE: 8

Ser Phe Asn Pro Val Tyr Pro Tyr Glu Asp Glu Ser Met Arg Arg Ala
1               5                   10                  15

His His Arg Arg Arg Arg Ala Ser His Arg
            20                  25

<210> SEQ ID NO 9
<211> LENGTH: 25
<212> TYPE: PRT
<213> ORGANISM: Artificial Sequence
<220> FEATURE:
<223> OTHER INFORMATION: hybrid peptide

<400> SEQUENCE: 9

Ser Phe Asn Pro Val Tyr Pro Tyr Glu Asp Glu Ser Gly Arg Arg Arg
1               5                   10                  15

Lys Arg Thr Ala Thr Arg Arg Ser
            20                  25
```